(12) United States Patent
Denny et al.

(10) Patent No.: US 9,566,395 B2
(45) Date of Patent: Feb. 14, 2017

(54) MEDICAMENT STORAGE, DISPENSING, AND ADMINISTRATION SYSTEM AND METHOD

(71) Applicant: Mylan Inc., Morgantown, WV (US)

(72) Inventors: John W. Denny, Cary, NC (US); Kevin Ostrander, Ringoes, NJ (US)

(73) Assignee: Mylan Inc, Canonsburg, PA (US)

(*) Notice: Subject to any disclaimer, the term of this patent is extended or adjusted under 35 U.S.C. 154(b) by 0 days.

(21) Appl. No.: 14/715,518

(22) Filed: May 18, 2015

(65) Prior Publication Data

US 2015/0251839 A1 Sep. 10, 2015

Related U.S. Application Data

(63) Continuation of application No. PCT/US2013/072878, filed on Dec. 3, 2013.
(Continued)

(51) Int. Cl.
*G08B 21/00* (2006.01)
*A61M 5/50* (2006.01)
(Continued)

(52) U.S. Cl.
CPC ........ *A61M 5/5086* (2013.01); *A61B 50/3001* (2016.02); *A61J 7/0076* (2013.01);
(Continued)

(58) Field of Classification Search
CPC ..... H04W 64/00; H04W 48/04; B67D 7/3236; G08B 21/16; G08B 3/10; G08B 5/36; A61M 5/002; A61M 2205/3553; A61M 2205/3569; A61M 2205/3584; G06F 19/323
(Continued)

(56) References Cited

U.S. PATENT DOCUMENTS

| 4,031,893 A | 6/1977 | Kaplan et al. |
| 4,394,863 A | 7/1983 | Bartner |

(Continued)

FOREIGN PATENT DOCUMENTS

| CN | 1761965 | 4/2006 |
| CN | 101495080 | 7/2009 |

(Continued)

OTHER PUBLICATIONS

International Search Report and Written Opinion dated Jun. 26, 2015 in PCT/US15/21658.
(Continued)

*Primary Examiner* — George Bugg
*Assistant Examiner* — Anthony D Afrifa-Kyei (57) ABSTRACT

Various exemplary embodiments relate to an electronic device for dispensing a medicament. The electronic device may include a medicament storage case or an electronic medicament device. The medicament storage case includes: a door moveable between an open position and a closed position; a lock moveable between a locked position where the lock maintains the door in the closed position and an unlocked position where the lock allows the door to move to the open position; a medicament dispensing device containing medication; an input device located on an external surface of the storage case activatable by a user; a communication unit configured to initiate a two-way communication between the user and a remote access control center upon activation of the input device and configured to receive an access signal from the remote access control center; and an actuator responsive to the access signal to move the lock to the open position upon receipt of the communication from the remote access control center. The electronic medicament device includes a reservoir configured to store an amount of medication, an administration component for administering
(Continued)

the medication to a patient, and a processor communicatively connected to a memory.

20 Claims, 6 Drawing Sheets

Related U.S. Application Data (60) Provisional application No. 61/732,753, filed on Dec. 3, 2012.

(51) Int. Cl.
*A61M 5/20* (2006.01)
*B65D 83/02* (2006.01)
*A61J 7/00* (2006.01)
*G08B 1/08* (2006.01)
*H04M 3/51* (2006.01)
*A61M 5/00* (2006.01)
*G06F 19/00* (2011.01)
*G08B 3/10* (2006.01)
*G08B 5/36* (2006.01)
*G08B 21/18* (2006.01)

(52) U.S. Cl.
CPC .............. *A61M 5/002* (2013.01); *A61M 5/20* (2013.01); *B65D 83/02* (2013.01); *G06F 19/323* (2013.01); *G06F 19/3456* (2013.01); *G06F 19/3462* (2013.01); *G06F 19/3468* (2013.01); *G08B 1/08* (2013.01); *G08B 3/10* (2013.01); *G08B 5/36* (2013.01); *G08B 21/182* (2013.01); *H04M 3/5116* (2013.01); *A61M 2205/18* (2013.01); *A61M 2205/3306* (2013.01); *A61M 2205/3368* (2013.01); *A61M 2205/3553* (2013.01); *A61M 2205/3569* (2013.01); *A61M 2205/3584* (2013.01); *A61M 2205/3592* (2013.01); *A61M 2205/52* (2013.01); *A61M 2205/581* (2013.01); *A61M 2205/6054* (2013.01); *A61M 2205/6072* (2013.01)

(58) Field of Classification Search
USPC .......................... 340/539.13, 539.12, 686.6
See application file for complete search history.

(56) References Cited

U.S. PATENT DOCUMENTS

| | | | |
|---|---|---|---|
| 4,484,910 A | 11/1984 | Sarnoff et al. | |
| 4,640,686 A | 2/1987 | Dalling et al. | |
| 4,663,621 A | 5/1987 | Field et al. | |
| 4,678,461 A | 7/1987 | Mesa | |
| 4,695,954 A | 9/1987 | Rose | |
| 4,731,765 A | 3/1988 | Cole et al. | |
| 4,795,433 A | 1/1989 | Sarnoff | |
| 4,832,682 A | 5/1989 | Sarnoff | |
| 4,959,358 A | 9/1990 | Carey | |
| 5,085,641 A | 2/1992 | Sarnoff et al. | |
| 5,092,843 A | 3/1992 | Monroe et al. | |
| 5,102,393 A | 4/1992 | Sarnoff et al. | |
| 5,205,436 A | 4/1993 | Savage | |
| 5,205,628 A | 4/1993 | Swets | |
| 5,221,024 A | 6/1993 | Campbell | |
| 5,346,297 A | 9/1994 | Colson, Jr. | |
| 5,354,286 A | 10/1994 | Mesa et al. | |
| 5,564,803 A | 10/1996 | McDonald | |
| 5,710,551 A | 1/1998 | Ridgeway | |
| 5,815,586 A | 9/1998 | Dobbins | |
| 5,819,981 A | 10/1998 | Cox | |
| 5,835,455 A | 11/1998 | Hanson et al. | |
| 5,905,653 A | 5/1999 | Higham | |
| 5,912,818 A | 6/1999 | McGrady | |
| 5,914,675 A | 6/1999 | Tognazzini | |
| 5,955,947 A | 9/1999 | Sutsos et al. | |
| 5,967,975 A | 10/1999 | Ridgeway | |
| 6,011,999 A | 1/2000 | Holmes | |
| 6,032,155 A | 2/2000 | De La Huerga | |
| 6,109,774 A | 8/2000 | Holmes et al. | |
| 6,131,399 A | 10/2000 | Hall | |
| 6,151,536 A | 11/2000 | Arnold | |
| 6,158,613 A | 12/2000 | Novosel et al. | |
| 6,216,925 B1 | 4/2001 | Garon | |
| 6,259,356 B1 | 7/2001 | Tamaoki | |
| 6,401,991 B1 | 6/2002 | Eannone et al. | |
| 6,471,087 B1 | 10/2002 | Shusterman | |
| 6,529,446 B1 | 3/2003 | De La Huerga | |
| 6,595,362 B2 | 7/2003 | Penney et al. | |
| 6,633,796 B1 | 10/2003 | Pool et al. | |
| 6,707,763 B2 | 3/2004 | Osberg et al. | |
| 6,825,753 B2 | 11/2004 | Cardinale et al. | |
| 6,880,722 B2 | 4/2005 | Anderson et al. | |
| 6,937,150 B2 | 8/2005 | Medema et al. | |
| 6,941,274 B1 | 9/2005 | Ramachandran et al. | |
| 6,958,691 B1 | 10/2005 | Anderson et al. | |
| 7,032,752 B2 | 4/2006 | Krackow | |
| 7,077,286 B2 | 7/2006 | Shows | |
| 7,138,902 B2 | 11/2006 | Menard | |
| 7,155,306 B2 | 12/2006 | Haitin | |
| 7,191,777 B2 | 3/2007 | Brand | |
| 7,449,012 B2 | 11/2008 | Young et al. | |
| 7,715,277 B2 | 5/2010 | de la Huerga | |
| 7,731,686 B2 | 6/2010 | Edwards | |
| 7,749,194 B2 | 7/2010 | Edwards et al. | |
| 7,819,116 B2 | 10/2010 | Brand | |
| 7,941,534 B2 | 5/2011 | de la Huerga | |
| 7,996,106 B2 | 8/2011 | Ervin | |
| 8,021,344 B2 | 9/2011 | Edwards | |
| 8,044,778 B2 | 10/2011 | Monroe | |
| 8,048,035 B2 | 11/2011 | Mesa et al. | |
| 8,149,111 B2 | 4/2012 | Monroe | |
| 8,172,082 B2 | 5/2012 | Edwards et al. | |
| 8,206,360 B2 | 6/2012 | Edwards | |
| 8,226,610 B2 | 7/2012 | Edwards | |
| 8,361,026 B2 | 1/2013 | Edwards | |
| 8,423,180 B1 | 4/2013 | Frederick | |
| 8,487,738 B2 | 7/2013 | Faries et al. | |
| 8,544,645 B2 | 10/2013 | Edwards et al. | |
| 8,593,278 B2 | 11/2013 | Churbock et al. | |
| 8,670,865 B2 | 3/2014 | Coe | |
| 8,744,620 B2 | 6/2014 | Shavelsky et al. | |
| 8,753,308 B2 | 6/2014 | Palmer et al. | |
| 8,922,367 B2 | 12/2014 | Denny et al. | |
| 2001/0028308 A1 | 10/2001 | De La Huerga | |
| 2001/0032035 A1 | 10/2001 | Holmes | |
| 2002/0100472 A1 | 8/2002 | Casper et al. | |
| 2002/0173875 A1 | 11/2002 | Wallace | |
| 2002/0179622 A1 | 12/2002 | Mase | |
| 2002/0188259 A1* | 12/2002 | Hickle | A61M 16/183 604/189 |
| 2003/0023146 A1 | 1/2003 | Shusterman | |
| 2003/0023345 A1 | 1/2003 | Depeursinge | |
| 2003/0090364 A1 | 5/2003 | Cardinale et al. | |
| 2003/0174554 A1 | 9/2003 | Dunstone | |
| 2004/0099676 A1 | 5/2004 | Anderson et al. | |
| 2004/0108795 A1 | 6/2004 | Meek, Jr. | |
| 2004/0158350 A1 | 8/2004 | Ostergaard et al. | |
| 2004/0173561 A1 | 9/2004 | Wolfe | |
| 2005/0005934 A1 | 1/2005 | Harvey | |
| 2005/0023286 A1 | 2/2005 | Pinney | |
| 2005/0113969 A1 | 5/2005 | Spano, Jr. | |
| 2005/0146419 A1 | 7/2005 | Porter | |
| 2005/0192705 A1 | 9/2005 | Pinney | |
| 2005/0236418 A1 | 10/2005 | Baker | |
| 2005/0258066 A1 | 11/2005 | Conley | |
| 2006/0030891 A1 | 2/2006 | Saltzstein et al. | |
| 2006/0058724 A1 | 3/2006 | Handfield | |
| 2006/0089545 A1 | 4/2006 | Ratjen et al. | |
| 2006/0125356 A1 | 6/2006 | Meek, Jr. | |
| 2006/0139148 A1 | 6/2006 | Faro | |
| 2006/0139149 A1 | 6/2006 | Faro | |

(56) References Cited

U.S. PATENT DOCUMENTS

| | | |
|---|---|---|
| 2006/0253096 A1 | 11/2006 | Blakley |
| 2007/0125100 A1 | 6/2007 | Schoenfeld et al. |
| 2007/0129708 A1* | 6/2007 | Edwards et al. ............ 604/890.1 |
| 2007/0185615 A1 | 8/2007 | Bossi |
| 2007/0186923 A1 | 8/2007 | Poutiatine et al. |
| 2007/0197968 A1 | 8/2007 | Pongpairochana et al. |
| 2007/0204497 A1* | 9/2007 | de la Huerga ................. 40/630 |
| 2007/0208598 A1 | 9/2007 | McGrady |
| 2007/0215018 A1 | 9/2007 | Faries, Jr. |
| 2007/0221680 A1 | 9/2007 | Yuyama |
| 2007/0227204 A1 | 10/2007 | Shoenfeld |
| 2007/0233001 A1 | 10/2007 | Burroughs et al. |
| 2007/0241122 A1 | 10/2007 | Yuyama |
| 2007/0244598 A1 | 10/2007 | Shoenfeld |
| 2007/0262084 A1 | 11/2007 | Yuyama |
| 2007/0272746 A1* | 11/2007 | Ortiz ..................... G06K 17/00 235/385 |
| 2007/0285238 A1* | 12/2007 | Batra ..................... G01K 1/024 340/572.1 |
| 2008/0030345 A1* | 2/2008 | Austin ................... A61B 90/98 340/572.8 |
| 2008/0059228 A1 | 3/2008 | Bossi |
| 2008/0188813 A1 | 8/2008 | Miller et al. |
| 2008/0202978 A1 | 8/2008 | Saloman et al. |
| 2008/0203107 A1 | 8/2008 | Conley |
| 2008/0249468 A1 | 10/2008 | Edwards et al. |
| 2008/0264962 A1 | 10/2008 | Schifman |
| 2009/0030366 A1 | 1/2009 | Hochman |
| 2009/0040874 A1 | 2/2009 | Rooney |
| 2009/0120962 A1 | 5/2009 | Malorni et al. |
| 2009/0128330 A1* | 5/2009 | Monroe ..................... 340/568.1 |
| 2009/0149894 A1 | 6/2009 | Merry et al. |
| 2009/0164042 A1 | 6/2009 | Handfield |
| 2009/0184022 A1 | 7/2009 | Coe et al. |
| 2009/0187274 A1 | 7/2009 | Higham |
| 2009/0194104 A1 | 8/2009 | Van Sickle et al. |
| 2009/0231132 A1 | 9/2009 | Shoenfeld |
| 2009/0294521 A1 | 12/2009 | De La Huerga |
| 2010/0010666 A1 | 1/2010 | Adams |
| 2010/0022953 A1 | 1/2010 | Bochenko et al. |
| 2010/0022987 A1 | 1/2010 | Bochenko et al. |
| 2010/0062748 A1 | 3/2010 | Steinmetz |
| 2010/0160857 A1 | 6/2010 | Pongpairochana et al. |
| 2010/0169111 A1 | 7/2010 | Brue et al. |
| 2010/0204659 A1 | 8/2010 | Bochenko et al. |
| 2010/0211005 A1 | 8/2010 | Edwards et al. |
| 2010/0252036 A1 | 10/2010 | Sutherland et al. |
| 2010/0300130 A1 | 12/2010 | Shoenfeld |
| 2010/0305750 A1 | 12/2010 | Conley |
| 2010/0318035 A1 | 12/2010 | Edwards et al. |
| 2011/0148624 A1* | 6/2011 | Eaton ..................... H04W 4/028 340/539.13 |
| 2011/0166700 A1 | 7/2011 | Dunn |
| 2011/0234419 A1 | 9/2011 | Churbock et al. |
| 2011/0266929 A1 | 11/2011 | Michael |
| 2012/0003928 A1 | 1/2012 | Geboers |
| 2012/0012606 A1 | 1/2012 | Longley |
| 2012/0130534 A1 | 5/2012 | Wurm |
| 2012/0232693 A1 | 9/2012 | Allinson |
| 2012/0248947 A1 | 10/2012 | Kijowski |
| 2012/0253837 A1 | 10/2012 | Cashman |
| 2012/0259456 A1 | 10/2012 | Saltsov |
| 2012/0259458 A1 | 10/2012 | Barrett et al. |
| 2012/0274196 A1 | 11/2012 | Arceta et al. |
| 2012/0278228 A1 | 11/2012 | Rubinstein |
| 2012/0280815 A1 | 11/2012 | Edwards |
| 2012/0310410 A1 | 12/2012 | Adams |
| 2013/0006415 A1 | 1/2013 | Paydar |
| 2013/0030566 A1 | 1/2013 | Shavelsky et al. |
| 2013/0090594 A1 | 4/2013 | Palmer |
| 2013/0092702 A1 | 4/2013 | Holmes |
| 2013/0131586 A1 | 5/2013 | Poutiatine et al. |
| 2013/0166066 A1 | 6/2013 | Dunn |
| 2013/0320032 A1 | 12/2013 | Rahilly |
| 2014/0004808 A1* | 1/2014 | Li ............................ H01Q 1/22 455/90.2 |
| 2014/0114277 A1 | 4/2014 | Eggert et al. |
| 2014/0155827 A1 | 6/2014 | Ostrander et al. |
| 2014/0245697 A1 | 9/2014 | Omura |
| 2014/0252927 A1 | 9/2014 | Denny |
| 2014/0357304 A1 | 12/2014 | Ostrander et al. |
| 2014/0379874 A1 | 12/2014 | Starr et al. |
| 2015/0078536 A1 | 3/2015 | Denny |
| 2015/0080806 A1* | 3/2015 | Pribitkin ............. A61M 5/2033 604/189 |
| 2015/0105903 A1 | 4/2015 | Denny |

FOREIGN PATENT DOCUMENTS

| | | |
|---|---|---|
| EP | 1 291 802 | 3/2003 |
| HK | 1215666 | 9/2016 |
| IN | 1571/MUMNP/2015 A | 5/2016 |
| TW | 201633250 | 9/2016 |
| WO | WO 96/21925 | 7/1996 |
| WO | WO 03/043684 | 5/2003 |
| WO | WO 2005 004961 | 1/2005 |
| WO | WO 2007/081947 | 7/2007 |
| WO | 2008091838 A2 | 7/2008 |
| WO | 2010098931 A1 | 9/2010 |
| WO | 2016099934 A1 | 6/2016 |

OTHER PUBLICATIONS

International Search Report for PCT/US2013/072881 dated Feb. 26, 2014.

International Search Report for PCT/US2013/072878 dated Feb. 26, 2014.

International Search Report in Related PCT Application PCT/US2015/063808 dated Apr. 5, 2016, 3 pages.

Written Opinion in Related PCT Application PCT/US2015/063808 dated Apr. 5, 2016, 7 pages.

Extended Search Report in Related EP Application 13860009 dated Jul. 29, 2016, 9 pages.

* cited by examiner

MEDICAMENT STORAGE, DISPENSING, AND ADMINISTRATION SYSTEM AND METHOD

CROSS REFERENCE TO RELATED APPLICATIONS

This application is a continuation of U.S. patent application No. PCT/US2013/072878, filed Dec. 3, 2013, which claims the benefit of U.S. Provisional Application No. 61/732,753, filed on Dec. 3, 2012.

TECHNICAL FIELD

Various exemplary embodiments disclosed herein relate generally to storage, distribution, and administration of medicaments.

BACKGROUND

Some people suffer from medical conditions such as severe allergies that may result in anaphylaxis. Anaphylaxis may be treated by administration of epinephrine. Patients may be prescribed an auto-injector of epinephrine to treat sudden anaphylaxis.

Anaphylaxis, however, often leads to an emergency situation wherein epinephrine or other medication should be administered as soon as possible to prevent loss of life or other complications. It cannot be guaranteed that in all such situations, a patient entering anaphylactic shock is currently in possession of their prescribed auto-injector or has been previously prescribed an auto-injector at all. Further, in some cases, such as when the patient is a child, administration should be supervised or otherwise guided to prevent misuse. Again, in an emergency situation, a supervisor knowledgeable in the administration of the medication may not be available.

SUMMARY

In light of the present need for various contingency plans in the administration of epinephrine and other medications, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to a medicament storage case. The medicament storage case includes: a door moveable between an open position and a closed position; a lock moveable between a locked position where the lock maintains the door in the closed position and an unlocked position where the lock allows the door to move to the open position; a medicament dispensing device containing medication; an input device located on the storage case activatable by a user; a communication unit configured to initiate a two-way communication between the user and a remote access control center upon activation of the input device and configured to receive an access signal from the remote access control center; and an actuator responsive to the access signal to move the lock to the open position upon receipt of the communication from the remote access control center.

In various embodiments, the medicament storage case further includes a global positioning system (GPS) receiver configured to generate location information for the storage case, wherein the communication unit is further configured to communicate the location information to emergency responders.

In various embodiments, the medicament storage case is mounted to a wall.

In various embodiments, the user is not required to provide any identification or authorization credential.

In various embodiments, the medicament storage case receives information and generates a local access signal.

In various embodiments, the communication unit includes a connection to an internet.

In various embodiments, the medicament storage case further includes a plurality of medicament locks that each retain a medicament dispensing device and the access signal unlocks a single medicament lock.

In various embodiments, the medicament storage case reads an expiration date from the medicament device.

In various embodiments, the medicament dispensing device is an auto-injector.

Various embodiments relate to system including: a lockable medicament storage container comprising a medicament dispensing device and a communication unit; and a central access control terminal in two-way communication with the lockable medicament storage container and configured to remotely unlock the medicament storage container based on input from a human operator.

In various embodiments, the lockable medicament storage container further comprises a global positioning system (GPS) receiver configured to generate location information, wherein the communication unit is configured to transmit the location information to an emergency response system.

In various embodiments, the lockable medicament storage container is operable by an unregistered user.

Various embodiments relate to a method of unlocking a medicament storage case. The method includes: receiving, at a central access control terminal, a communication initiation from a remote medicament storage case; facilitating a two-way communication between a user of the remote medicament storage case and an operator of the central access control terminal; determining whether the medicament storage case contains a medicament dispensing device for treating a condition of the user or a patient; and transmitting an access signal to the medicament storage case to unlock a portion of the medicament storage case containing the medicament dispensing device for treating the condition of the user or the patient.

In various embodiments, the method further includes: receiving a GPS location from the medicament storage case; and forwarding the GPS location information to an emergency responder in the vicinity of the medicament storage case.

In various embodiments, the method further includes: providing instructions for using the medicament dispensing device.

In various embodiments, the instructions are at least one of audio instructions and video instructions.

In various embodiments, the method further includes performing a remote medical diagnosis of the patient based on the two-way communication.

In various embodiments, the method further includes: accessing a medical record of the patient. Various exemplary embodiments relate to an electronic medicament device including: a reservoir configured to store an amount of medication; an administration component for administering the medication to a patient; and a processor communicatively connected to a memory. In various embodiments, the administration component is an auto-injector.

Various embodiments are described wherein the electronic medicament device additionally includes at least one of a display, a speaker, a communications interface, a GPS device, and an ID tag to be read by another device. In such embodiments, the processor may be configured to communicate the expiration of the medication via the display, provide audio administration instructions via the speaker, or communicate the occurrence of events (such as expiration or administration) to a remote device. In some embodiments, the processor may be configured to control the amount of medication administered to a patient based on information such as a locally-stored or remotely-retrieved patient record or patient information manually input into the electronic medicament device such as gender, age, and/or weight.

BRIEF DESCRIPTION OF THE DRAWINGS

In order to better understand various exemplary embodiments, reference is made to the accompanying drawings, wherein.

DETAILED DESCRIPTION

Referring now to the drawings, in which like numerals refer to like components or steps, there are disclosed broad aspects of various exemplary embodiments.

Figure 1:
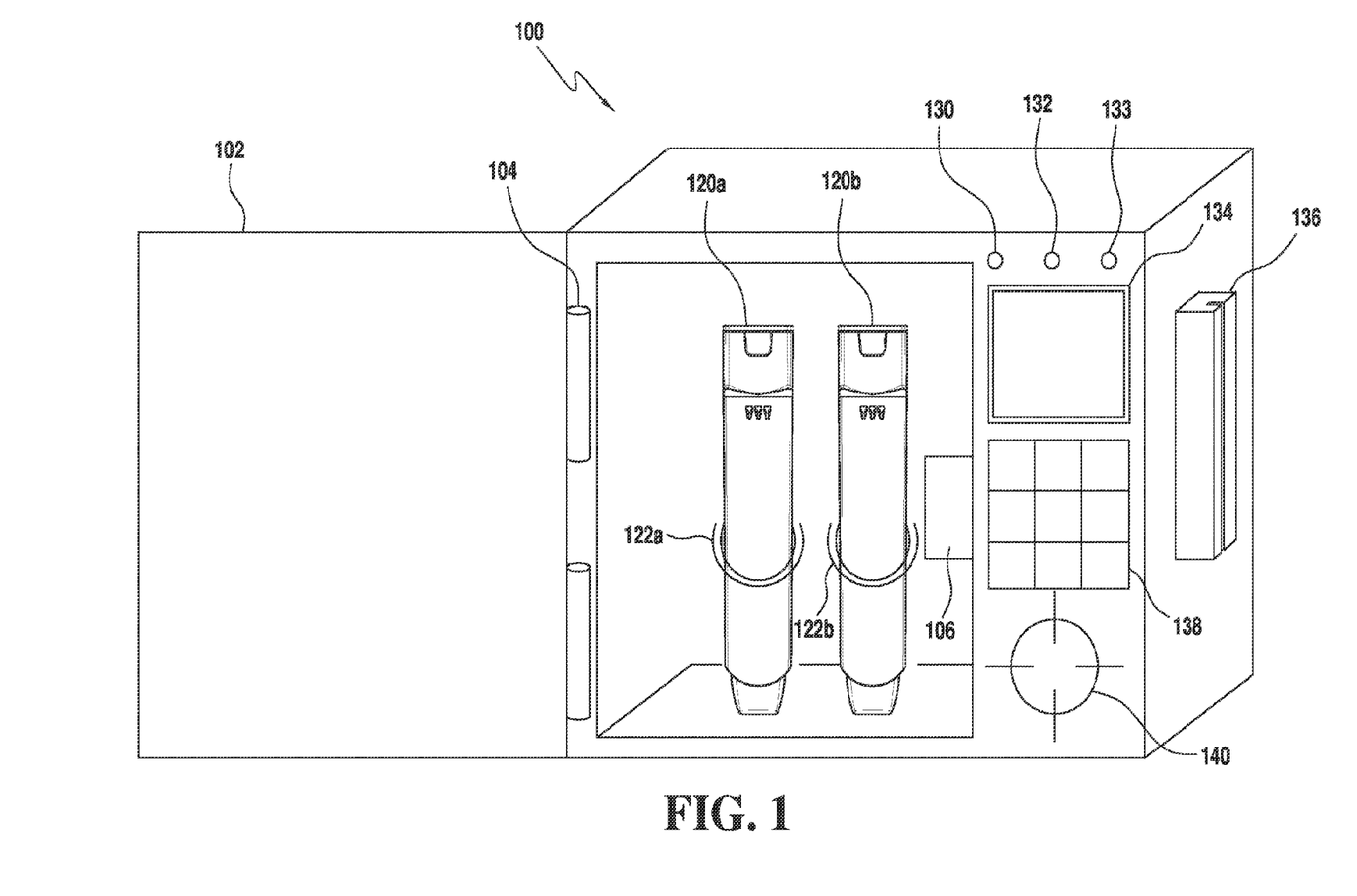
FIG. 1 illustrates an exemplary medicament storage case.

FIG. 1 illustrates an exemplary medicament storage case 100. The medicament storage case 100 may be used to provide a secure storage location for emergency medications such as, for example, auto-injectors of epinephrine. Medicament storage case 100 may be placed in a location where emergency medications may be needed. For example, medicament storage case 100 may be located in a school, church, child care facility, mass transit facility (such as an airport or train station), or vehicle. The medicament storage case 100 may be secured to a wall or other immovable object using any known securing hardware to prevent theft and tampering. The medicament storage case 100 may be accessed by an authorized person or patient to obtain prescription medication for the patient. The medicament storage case 100 may also facilitate communication with a central control center where an operator may remotely provide access to the medication. Medicament storage case 100 may include a door 102, hinges 104, lock 106, medicaments 120, medicament locks 122, camera 130, microphone 132, speaker 133, display 134, card reader 135, and wireless reader 140. Although not shown, the medicament storage case 100 may include various additional electronic components such as, for example, a processor, memory, and network interface, as will be described in greater detail below with respect to FIG. 2.

Door 102 is secured to case 100 by hinges 104. Hinges 104 allow door 102 to move between an open position and a closed position. Hinges 104 may be resistant to tampering. For example, hinges 104 may be mounted to an internal surface of case 100 such that access to hinges 104 is prevented when case 100 is closed and locked. Alternatively, door 102 may be a sliding door secured to case 100 by rails or other known door, window, or access panel arrangement. In another alternative, door 102 may be manufactured from glass or other clear frangible material that may be broken in case of emergency. Breaking the frangible material may result in actuation of the storage case 100, including actuation of the communication unit 230.

Lock 106 may include any lock for mechanically securing the door 102 in a closed position. For example, lock 106 may be of the dead bolt variety and engage a recess on door 102. Lock 106 may include an actuator for moving the lock 106 between a locked position and an unlocked position. For example, lock 106 may include a solenoid that moves lock 106 when energized. The actuator may include an authentication circuit that verifies an access signal. If the authentication circuit verifies an access signal, the actuator may move lock 106 to an unlocked position. If an incorrect access signal is received, the lock 106 may remain in a locked position. Alternatively, the lock 106 may not verify an access signal and instead may be controlled by another component, such as a processor.

Medicaments 120 may include one or more medicaments for treating emergency or other medical conditions. In various exemplary embodiments, medicaments 120 may be auto-injectors for administering a dose of epinephrine. Other suitable medicaments may include, but are not limited to, adrenergic agonists, antihistamines (e.g. diphenhydramine, hydroxyzine); $H_2$ receptor antagonists (e.g. cimetidine, ranitidine, and famotidine), bronchodilators (e.g. albuterol), corticosteroids (e.g. prednisone), positive inotropic agents (e.g. glucagon and insulin), opioid antagonists (e.g. naloxone), and other medicaments for use in emergency conditions (e.g. N-acetylcysteine). Suitable auto-injectors and associated devices and method are described by U.S. Pat. Nos. 4,031,893; 4,394,863; 4,484,910; 4,640,686; 4,678,461; 4,795,433; 4,832,682; 5,085,641; 5,092,843; 5,102,393; 5,354,286; 7,449,012; and 8,048,035, all of which are hereby incorporated by reference in their entireties for all purposes. Medicaments 120 may also include electronic auto-injectors described in further detail below with reference FIG. 3. Medicaments 120 may treat different conditions or provide different doses of medication. For example, medicament 120a may provide a larger dose than that provided by medicament 120b or may include a different medication from that included in medicament 120b. It will be apparent that, while two medicaments 120 are illustrated, a medicament storage case 100 may include a greater or fewer number of medicaments.

Medicament locks 122 may be additional locks that secure individual medicaments within case 100. Each medicament lock 122 may include an actuator that moves the medicament lock 122 into an unlocked position. As shown, medicament locks 122 may include a ring or cable that secure the medicament 120 to case 100. Alternatively, medicament locks 122 may include locking doors or drawers securing medicaments 120. Medicament locks 122 may require separate access conditions. For example, a first authorized patient may be able to access medicament 120a, but not medicament 120b, while a second authorized patient may be provided with access only to medicament 120b. Such access may be determined by locally- or remotely-stored prescription information or other patient records. Authorized emergency caregivers, such as medical professionals or on-site medical staff, may be provided with access to all medicaments 120 stored in the storage case 100.

Camera 130 may be a digital camera capable of recording video. As will be described in further detail below, camera 130 may be used to provide live video to an operator located at a remote facility. The video may be used to diagnose a patient or determine whether a request for the medicament is authentic. Camera 130 may be mounted to case 130 such that it is movable. For example, camera 130 may be attached with a hinge or pivot such that camera 130 may be manually moved to capture video of a subject. In various embodiments, the camera 130 and/or supporting structures may be provided with electrically operable mechanical devices, such as servo motors, such that the processor and/or remote operator may alter the position or orientation of the camera 130. In various embodiments, camera 130 may be mounted in a removable manner such that a subject out of view of case 100 may be viewed. Camera 130 may include a lock to prevent its removal. Camera 130 may be unlocked remotely by an operator.

Microphone 132 may record audio input. Microphone 132 may be used instead of, or in addition to, camera 130 to communicate with a remote operator. Microphone 132 may be integrated with camera 130.

Speaker 133 may provide audio output. Speaker 133 may be used to communicate with a remote operator and/or may play pre-recorded messages stored at case 100. For example, speaker 133 may play instructions for operating case 100, administering a medicament 120, or performing other emergency care. Speaker 133 may also output live instructions or other audio provided by the remote operator. In various embodiments, such as those embodiments to be deployed in noisy environments, the case may include one or more sets of headphones (not shown) in addition to, or in place of, speaker 133.

Display 134 may be an electronic display capable of showing video or images. For example, display 134 may be a liquid crystal display (LCD) or other computer monitor. Display 134 may display instructions or other information to a user such as video, images, and/or text demonstrating proper medication administration and/or emergency care. Such video, images, and/or text may be stored locally or transmitted from a remote location by a remote operator. Further, the video, text, and images may be displayed as part of a scripted sequence stored locally or at the instruction of a remote operator. For example, the remote operator may display a next image in a sequence once the operator has verified that a step associated with a currently-displayed image has been properly performed, may display a video that the operator has identified as relevant to a particular situation, or may type text for display to a hearing-impaired user. In various embodiments, display 134 may be a touch-screen display. A touch-screen display may be used as both a display and input device. Case 100 may also include an additional input device 138 such as a keyboard, keypad, mouse, and/or other known input devices. Display 134 or input device 138 may be used to enter information into case 100. For example, an authorized user may enter a security code for accessing case 100 or receiving information from case 100. As another example, a hearing-impaired user may type text messages that are subsequently transmitted to the remote operator. In various alternative embodiments, the display or input device may be located inside a first door of the storage device, separated from the medicament compartment by a second door, drawer or other medicament lock. A user would then open the first door to access the input device or display.

Card reader 135 may be a magnetic stripe reader for reading information from a card. For example, authorized users, such as patients and emergency caregivers, may be issued a card providing access to the storage case 100 along printed, electronically-stored, and/or magnetically stored prescription and/or patient information, such as patient records or a patient identifier. The card may be used to quickly input the user and/or patient information into case 100. Other types of card readers may include smart card readers, bar code scanners, quick response (QR) code scanners, or other devices for reading a token that identifies an individual.

Wireless reader 140 may be a device for reading and transmitting data via radio frequency identification (RFID), near field communication (NFC), Bluetooth, or other short range wireless communications. Wireless reader 140 may interact with wireless tags or devices located with case 100 or external to case 100. Internal wireless tags or devices may be included as part of the medicaments 120. As will be described in further detail below, medicaments 120 may include wireless tags that include information regarding the medicament. Wireless reader 140 may periodically poll the tags to acquire information regarding the medicaments. For example, the wireless reader 140 may read an expiration date from a tag carried by each medicament or may communicate with a separate processor of each medicament (as will be described in greater detail below) to retrieve a Boolean value indicating whether the medicament is currently expired. If a medicament 120 is expired, the case 100 may subsequently prevent the corresponding lock 122 from opening under any or most conditions and/or transmit a message, such as a message to the remote operator, that the medicament is expired and should be replaced.

External wireless tags may include identification cards of authorized users or patients. An RFID or NFC identification card may perform similar authorization functions to cards using card reader 136 as discussed above, either in addition to or as an alternative to the card reader 136. External wireless devices may include devices such as smart phones or other portable electronics. External wireless devices may include applications for monitoring medicament usage or providing access to case 100. Case 100 may provide information to an external wireless device via wireless reader 140.

Various additional means for confirming an identity of a user will be apparent. For example, the storage case 100 may include devices (not shown) for retrieving biometric data for a user. As such, the storage case 100 may include a fingerprint scanner, retina scanner, or other biometric information retrieval device. Additionally, or alternatively, the storage case 100 may retrieve a biometric-encoded password via the input device138. Upon retrieving an identifier for a user, such as an id string from a magnetic stripe or wireless communication chip or an id calculated from biometric data, the storage case 100 may transmit the ID to a remote operator and/or retrieve user authorization data or other user information. For example, the storage case 100 may locally store user information or may communicate with a remote database to retrieve the appropriate user information.

In various embodiments, the case 100 or a portion thereof may be climate controlled. For example, the case 100 may include a refrigerated compartment for storage of medicaments for administration of insulin. As another example, the case 100 may include devices for controlling the internal humidity, internal temperature and/or other climate conditions. Additional climate control devices will be apparent, including the appropriate sensors for measuring and reporting climate conditions.

Figure 2:
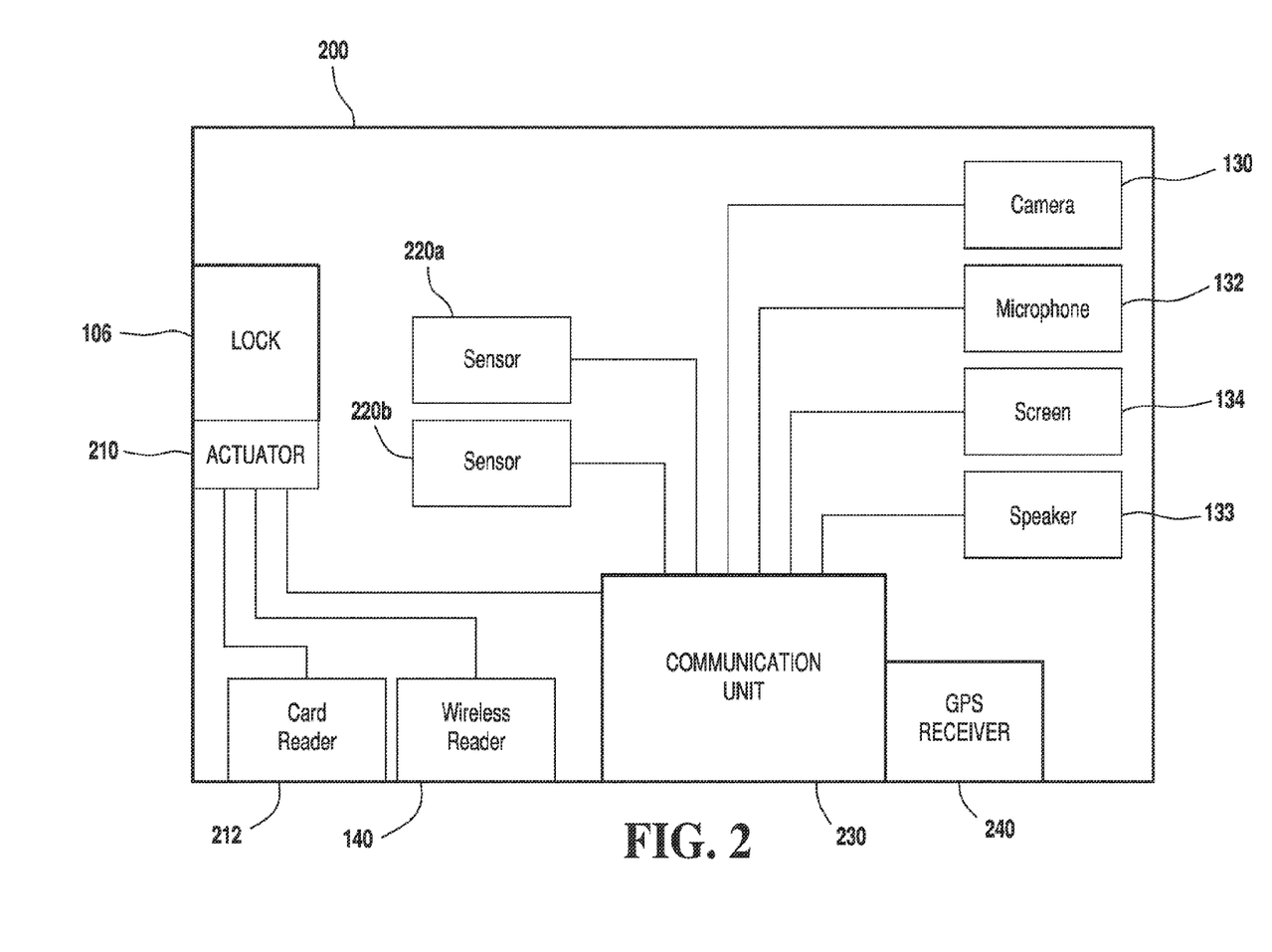
FIG. 2 illustrates a schematic diagram of the components of a medicament storage case.

FIG. 2 illustrates a schematic diagram 200 of the components of case 100. Schematic diagram 200 includes lock 106, camera 130, microphone 132, speaker 133, display 134, card reader 136, input device 138, wireless reader 140, actuator 210, sensors 220, communication unit 230, and global positioning system (GPS) receiver 240. Although not shown, the case 100 may include additional components such as a processor, memory, and/or storage device. Alternatively, such components may be included as part of and/or shared between those components that are illustrated. As used herein, the term "processor" will be understood to encompass various processing devices such as microprocessors, application-specific integrated circuits (ASICs), field-programmable gate arrays (FPGAs), and other processors. If included as a separate component, a processor (not shown) may interconnect the various components illustrated in FIG. 2.

Actuator 210 may be coupled to lock 106 such that actuator 210 may move lock 106 between a locked position and an unlocked position. Actuator 210 may receive a locally provided access signal from card reader 136, input device 138, wireless receiver 140, and/or a processor (not shown). The locally provided access signal may cause actuator 210 to unlock case 100 without prior communication to a control center.

Sensors 220a and b may provide monitoring of medicaments 120. Each medicament 120 may be equipped with a sensor 220. The sensor 220 may be integrated into a medicament lock 122. In various embodiments, sensors 220 may detect removal of the corresponding medicament 120 and provide an indication to communication unit 230. Communication unit 230 may report the removal of the medicament 120 to a control center. In various embodiments, sensors 220 may be implemented with wireless reader 140. Wireless reader 140 may periodically poll wireless tags attached to the medicament to collect information. Wireless reader 140 may determine if a medicament 120 has moved out of the wireless range or if the medicament 120 provides other key information such as expiration of the medicament. In various embodiments, the sensors may be further adapted to enable communication with one or more processors integrated into the medicaments 120.

The communication unit 230 may facilitate a two-way communication with a control center and provide a remote access signal from the control center. The communication unit 230 may include any device for communicating information from the case 100 to the control center such as a telephone or digital modem. Communication unit 230 may use wired (such as a phone line, Ethernet, or wired Internet connection) or wireless (such as wifi, mobile carrier network, or satellite) communication channels to communicate with the control center. The communication unit 230 may be in communication (such as directly or via a processor) to camera 130, microphone 132, speaker 133, and display 134 to provide a live audio/video communication session between a user of case 100 and an operator at the control center. The operator at the control center may gather information from and provide instructions to a user at the case 100. If the operator determines that access should be provided to a medicament, the operator may provide a remote access signal via the communication unit 230. The communication unit 230 may also provide any other information gathered by the components of case 100 to the control center. For example, a temperature sensor component of case 100 may send an alert to the control center that the internal temperature of the case is out of range and requires correction. The control center may then correct the temperature by use of the communication unit 230.

GPS receiver 240 may determine a physical location of case 100. In various embodiments, GPS receiver 240 receives signals from GPS satellites in order to calculate a location of case 110. In various alternative embodiments, GPS receiver 240 may include a memory for storing a location such that active communication with GPS satellites is not necessary. GPS receiver 240 may provide the location information to communication unit 230 so that it may be forwarded to a control center.

Figure 3:
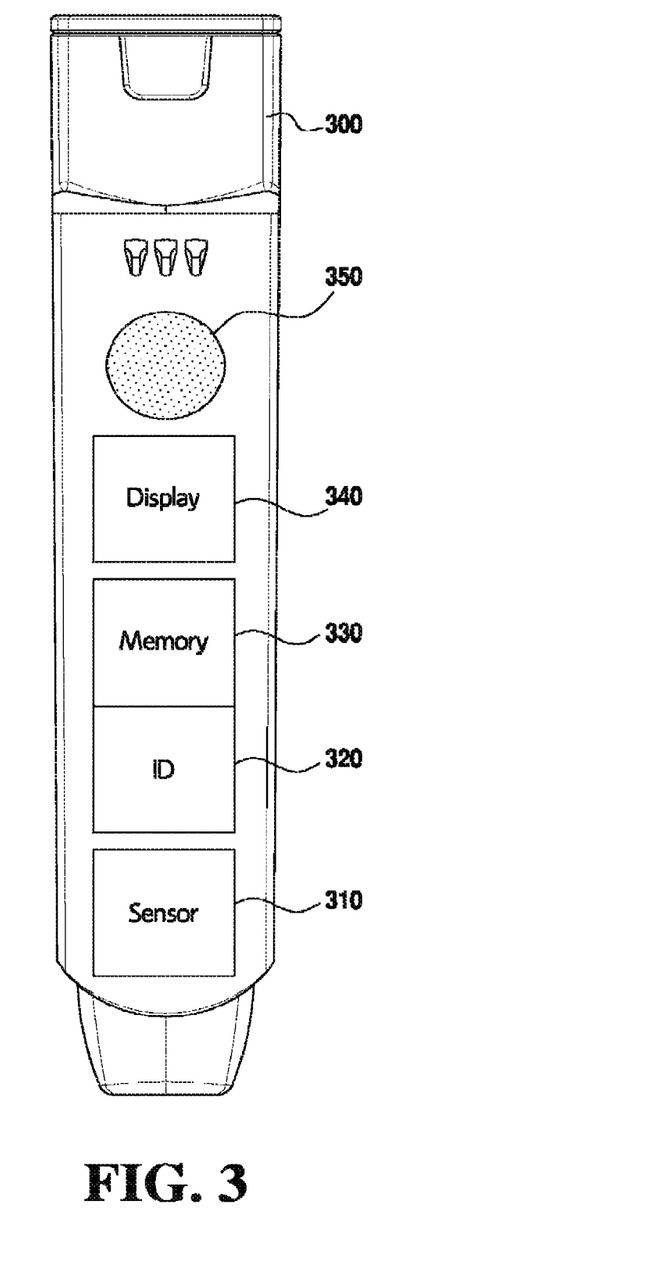
FIG. 3 illustrates an exemplary electronic medicament device.

FIG. 3 illustrates an exemplary electronic medicament device 300. The electronic medicament device 300 may include a medication for treating a condition, the medication being stored in a reservoir. In various exemplary embodiments, the electronic medicament device 300 includes an auto-injector for epinephrine or other administration component such as a non-auto-injector needle or controlled access panel for providing access to a solid medication stored in the reservoir. The electronic medicament device 300 may further include sensor 310, ID tag 320, memory 330, display 340, and speaker 350. Although not illustrated, the electronic medicament device may include additional hardware such as, for example, a processor and/or additional communication interfaces. A processor may interconnect one or more of those components illustrated in FIG. 3. Such additional communication interface may include, for example, an interface for communication via wifi, a mobile carrier network, or satellite. Alternatively, the additional communication interface may include a wired communication interface.

Sensor 310 may detect activation of electronic medicament device 300. Sensor 310 may include a frangible element that completes or breaks an electronic circuit when electronic medicament device 300 is activated. Sensor 310 may provide a signal to ID tag 320 to perform an action in response to use of the medicament. Sensor 310 may alter memory 330 to indicate that the medicament device 300 is used and may log a time of use.

ID tag 320 may include an RFID, NFC, or other tag for short range wireless communications. Such tags may be powered by passive energy and not require a battery. In various embodiments, ID tag 320 may include a battery powered wireless transmitter using, for example, Bluetooth. ID tag 320 may provide information from electronic medicament device 300 to a wireless reader such as, for example, wireless reader 140 or a NFC enabled mobile device. ID tag 320 may be connected to or include memory 330.

Memory 330 may store information regarding electronic medicament device 300. Memory 330 may include a non-volatile memory such as a read-only memory (ROM) or an electronically erasable programmable read only memory (EEPROM). Information stored by memory 330 may include manufacture date, expiration date, medication, dose size, audio instructions, text instructions, other instructions, prescription information, re-order information, and emergency contact information.

Display 340 may include a display such as a LCD, LED array, or a single LED. Display 340 may display information about electronic medicament device 300. Display 340 may read and display any information stored in memory 330. For example, display 340 may display the expiration date of the medication. Display 340 may also display instructions for a user. In various embodiments, display 340 may illuminate, flash, or display a particular message in response to particular events such as the expiration of the medication, use of the medicament, or separation from another device such as case 100 or a mobile device.

Speaker 350 may provide audio output. For example, speaker 350 may play pre-recorded instructions stored in memory 330. In various embodiments, ID tag320 or another communication interface (not shown) may download or stream information from another device to be played by speaker 350. For example, the electronic medicament device 300 may stream information from a storage case 100 or from a remote operator, either directly or via a storage case 100.

Various functions described above in connection with the storage case 100 may be provided directly on the electronic medicament device 300. For example, the electronic medicament device may include a microphone for transmitting audio to a remote operator, a GPS device for determining a current location, a keypad for inputting an authorization code, or any of the other components described above in connection with the storage case. As such, the electronic medicament device 300 may be provided and used in contexts that do not involve the storage case 100. For example, a physician or pharmacy may provide the electronic medicament device 300 directly to a patient for future use.

In various embodiments, the electronic medicament device 300 may be reusable. As such, the electronic medicament device 300 may receive a disposable cartridge or component set including the medication and/or a clean needle. Such cartridge or component set may include its own RFID tag or other means for communicating an expiration date or other information to the electronic medicament device 300 or a storage case 100.

In various embodiments, the processor or other component of the electronic medicament device 300 may alter the operation of the electronic medicament device 300 based on user information or other information. For example, the electronic medicament device 300 may provide different dosages based on a dosage prescribed to an authorized user. As another example, a user may input a patient weight into a keypad of the electronic medicament device 300. The processor may then calculate and administer an appropriate dosage based on the input weight. As another example, the processor may prevent or disable medicine administration when the user is not authorized for such administration.

Figure 4:
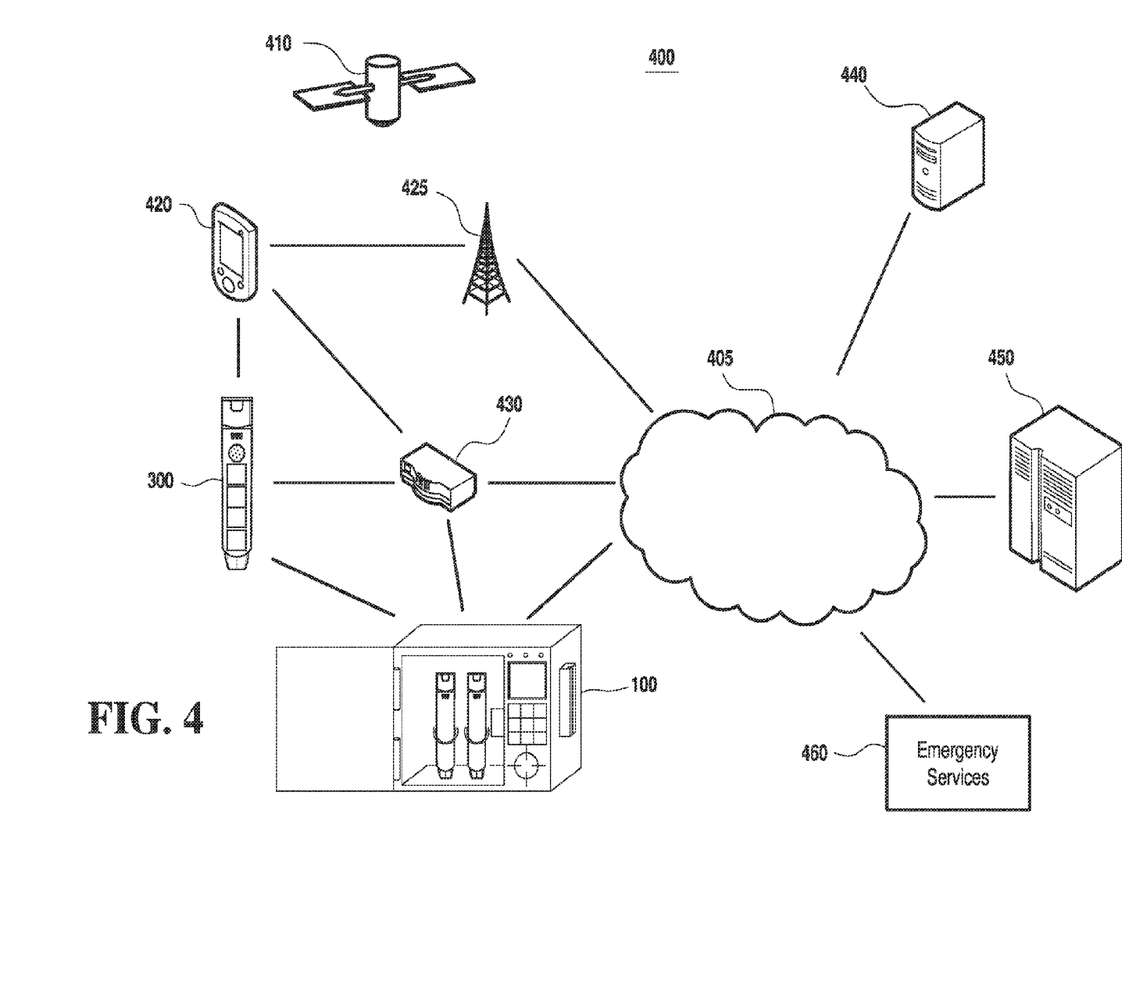
FIG. 4 illustrates an exemplary network environment for a medicament storage case and electronic medicament device.

FIG. 4 illustrates an exemplary network environment 400 for storage case 100 and electronic medicament device 300. Storage case 100 and electronic medicament device 300 may interact with various elements of network environment 400 to provide emergency access and enhanced features. Network environment 400 includes network 405, GPS satellites 410, mobile device 420, mobile base station 425, wireless router 430, medical server 440, central control 450, and emergency services 460.

Network 405 may be a digital network for communicating information. For example, network 405 may be the internet. Network 405 may transmit information between various end users and devices. Network 405 may also include telephone networks.

GPS satellites 410 may enable storage case 110, electronic medicament device 300, mobile device 420, and other devices to determine their respective physical locations. GPS satellites 410 may be geosynchronous satellites that broadcast signals. GPS enabled devices may use the signals from multiple satellites to determine their location. In various embodiments, GPS satellites 410 may include or be replaced by terrestrial location systems.

Mobile device 420 may be a device such as a smart phone, tablet computer, laptop, or any other computing device capable of executing applications and performing communication. In various embodiments, mobile device 420 is an NFC enabled mobile phone that can communicate using short range wireless protocols as well as local networking and mobile networks. In particular, mobile device 420 may communicate with a mobile network using mobile base station 425.

Mobile device 420 may interact with the storage case 100 and/or the electronic medicament device 300 using RFID, NFC, or other wireless communication. For example, the mobile device 420 may transmit a user identification to the storage case 100 or the electronic medicament device 300 for authorizing the holder of the mobile device 420 to access and/or administer the electronic medicament device. The mobile device 420 may automatically transmit the user identification, such as continuously or periodically, such that the user may be easily authorized in an emergency situation. In various alternative embodiments, the mobile device 420 may only transmit the user identification upon request by the user. Mobile device 420 may also act as an interface for accessing the storage case 100 and/or electronic medicament device 300. For example, mobile device 420 may allow for communication between the user and control center, thereby facilitating diagnosis if the user is not movable.

Mobile device 420 may include an application specifically for interacting with electronic medicament device 300. Mobile device 420 may access memory 330 via ID tag 320 and read or write data. Mobile device 420 may detect changes in electronic medicament device 300 and perform actions in response. For example, mobile device 420 may detect that electronic medicament device 300 has been activated. Mobile device 420 may automatically contact emergency services 460 and allow a user to speak with emergency personnel, or mobile device 420 may provide a pre-recorded message to emergency services 460 indicating that the medicament has been activated to treat a condition of the patient. Mobile device 420 may also provide a location based on GPS information so that emergency personnel can locate the patient.

ID tag 320 may be used to determine whether electronic medicament device 300 is within close proximity to a mobile device 420. ID tag 320 may periodically poll or be polled by a wireless reader in the mobile device 420. If the poll does not occur when expected, or the mobile device does not respond, electronic medicament device 300 may generate an alert. For example, electronic medicament device 300 may play a sound through the speaker 350 or flash the display 340 to alert a user. The alert may remind the user to keep the medicament close by in case of emergency. Mobile device 420 may also generate an alert if electronic medicament device 300 is not detected. Mobile device 420 may be configured to check for the presence of electronic medicament device 300 whenever the user enters or leaves a particular location. For example, mobile device 420 may generate an alert if a user leaves home without the electronic medicament device.

Mobile device 420 may also contact emergency contacts. For example, mobile device 420 may email, message, or call any emergency contacts stored in memory 330 or within mobile device 420 when the electronic medicament device 300 is used or generates some other alert. Mobile device 420 may select contacts based on time of day or other available information.

Upon detection of an expired medicament or activation of the medicament, mobile device 420 may initiate ordering a replacement medicament Mobile device 420 may send an order to either control center 450 or medical server 440. The order may include patient and prescription information. Medical server 440 may determine whether the prescription includes refills, whether replacements are allowed without a prescription, or whether the patient has a valid or perpetual prescription for the medicament. Medical server 440 may automatically fulfill the order if the prescription is authorized. Alternatively, medical server 440 may schedule an appointment with the patient's doctor for a new prescription and to follow-up regarding the deployment of the medicament.

Wireless router 430 may be a wireless router providing connectivity to a local area network (LAN) and the internet. Wireless router 430 may be accessed by storage case 100, electronic medicament device 300, and mobile device 420. Accordingly, wireless router 430 may provide these devices with internet access to send and receive data.

Medical server 440 may be a server operated by a health care provider or health insurance provider. Medical server 440 may store patient information. Medical server 440 may provide patient information to authorized devices such as the patient's mobile device 420, control center 450, and emergency services 460. Medical server 440 may be configured to receive and process particular messages from storage case 100, electronic medicament device 300, mobile device 420, and control center 450. For example, medical server 440 may be configured to verify prescriptions and order refills.

Control center 450 may include a server that communicates with one or more storage cases 100, electronic medicament devices 300, and/or mobile devices 420. Control center 450 may include an operator interface that allows an operator located at or in communication with control center 350 to communicate with a patient at a storage case 100. The control center may facilitate a two-way audio and/or video communication session between a user or patient at the storage case 100 and the operator. The operator may be able to diagnose the patient based on the two-way communication. The control center 450 may also receive information from storage case 100 such as available medicaments and location. If an operator of control center 450 determines that a medicament should be administered to a patient, control center 450 may generate a remote access signal to unlock storage case 100.

The control center 450 may communicate with medical server 440 to obtain medical information, such as prescriptions, regarding a patient. The control center 450 may communicate with emergency services 460 to provide patient information to emergency personnel. Additionally, the storage case 100 and/or electronic medicament device 300 may retrieve various user information from the medical server 440, the control center 450, or from other servers (not shown). For example, the storage case may retrieve patient records from the medical server 440 and user permissions from the control center 450.

It will be apparent that various additional devices may participate in exemplary network 400. For example, exemplary network 400 may include one or more servers for providing an application service to a user. For example, the electronic medicament device 300 may provide usage information to such an application server which, in turn, may process the data for various uses. For example, the application server may then provide the processed usage data to an application executing on a mobile device, such as mobile device 420. Such application may provide, for example a map indicating where the user has administered the electronic medicament device 300 and/or other electronic medicament devices 300. Such application could also present a real-time alert as to when the electronic medicament device 300 has been used, including location information. The application may also provide historical data and analysis of electronic medicament device 300 usage events such as event listings and graphs.

Figure 5:
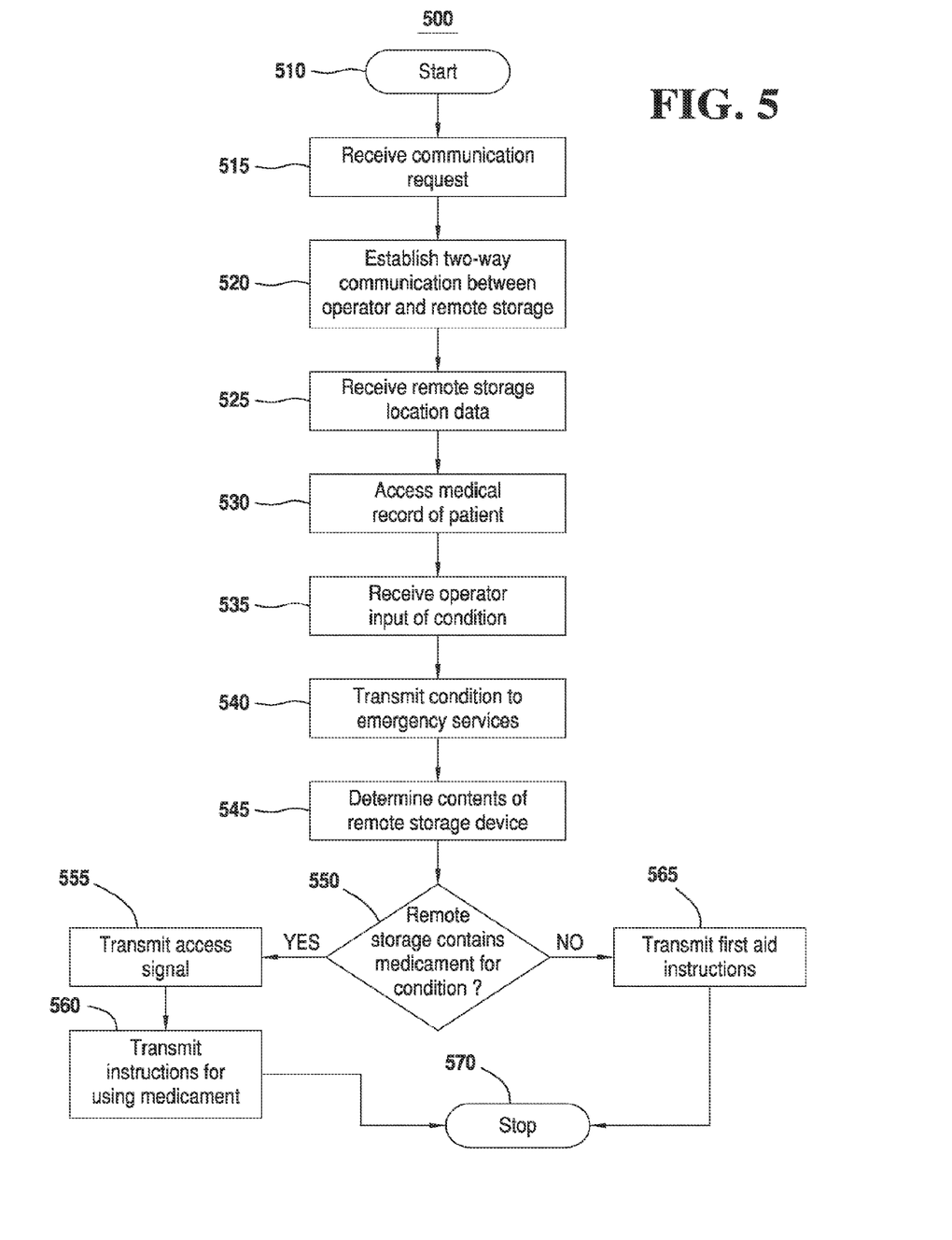
FIG. 5 illustrates a flowchart showing an exemplary method of providing remote access to a medicament.

FIG. 5 illustrates a flowchart showing an exemplary method 500 of providing remote access to a medicament. The method 500 may be performed by a control center 450. The method 500 may begin at step 510 and proceed to step 515.

In step 515, the control center 450 may receive a communication request from a remote medicament storage case 100. The control center 450 may determine an operator who is available to communicate with a potential patient. In step 520, the control center 450 may establish a two-way communication session between the selected operator and the remote storage case 100. In step 525, the control center 450 may also receive location information from the remote storage case 100. In step 530 the control center 450 may access a medical record of the patient based on an identifier provided to the operator by the patient through the two-way communication session or by the storage case 100 electronically. The patient may be identified using a card scanned at the storage case 100 or using the patient's name or other identifying information. The medical record may be retrieved from an internal database or may be provided by a medical server 440. In step 535, control center 450 may receive input of the patient's condition from the operator. Alternatively, the condition may be input at the storage case and approved by the operator. In step 540, control center 450 may transmit the patient's condition along with other information such as the patient's identity and location to emergency services 460. Emergency services 460 may be selected according to proximity to the patient. Control center 450 may also notify other emergency contacts if available from the patient's medical record or information received at the storage case. In step 545, control center 450 may determine the contents of the storage case 100. Control center 450 may receive a list of medicaments from the storage case 100. In step 550, control center 450 may determine whether the remote storage contains a medicament for the condition of the patient. Control center 450 may include a list of rules for comparing conditions and medicaments. Alternatively, the operator may determine whether any medicament is appropriate for treating the patient. If a medicament is available, the method 500 may proceed to step 550. If no medicament is available, the method 500 may proceed to step 565. In step 555, the control center 450 may transmit an access signal to storage case 100. The access signal may unlock the storage case 100 and/or a medicament lock 106 for the medicament. In step 560, the control center 450 may transmit instructions for administering the medicament. The instructions may be provided by the operator or may be pre-recorded instructions specific for the medicament. If the storage case 550 does not include an appropriate medicament, in step 565, the control center 450 may provide any relevant first aid instructions for the patient's condition. Control center 450 may maintain the communication session until emergency personal have arrived to assist the patient. The method may then proceed to step 570, where the method ends.

Figure 6:
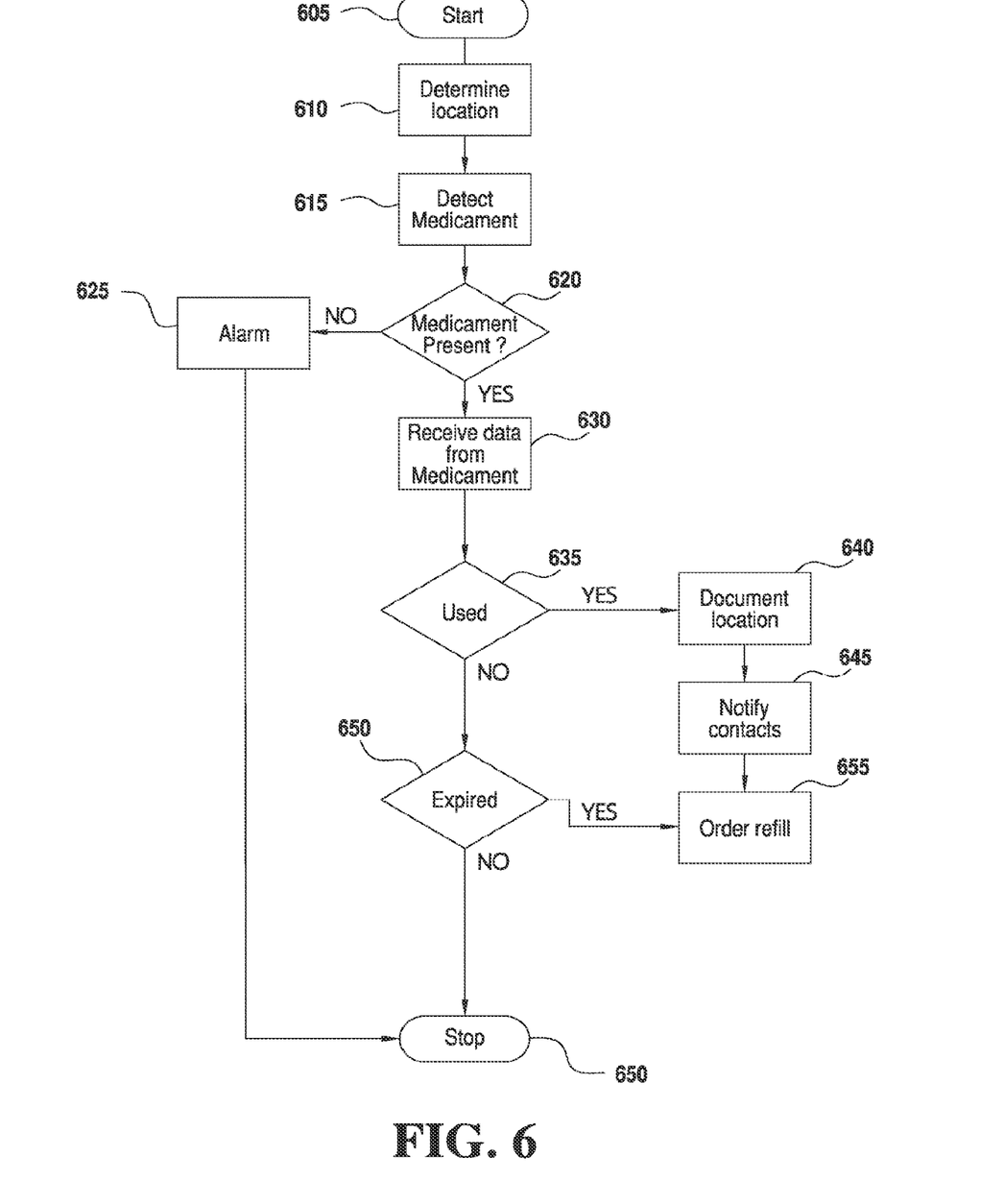
FIG. 6 illustrates a flowchart showing an exemplary method of monitoring a medicament.

FIG. 6 illustrates a flowchart showing an exemplary method 600 of monitoring a medicament. The method 600 may be performed by a mobile device 420 in communication with an electronic medicament device 300.

The method 600 may begin at step 605 and proceed to step 610. In step 610, the mobile device 420 may determine its location. In various embodiments, mobile device 420 may use the location to determine whether to proceed with the method. For example, the mobile device 420 may discontinue the method if the mobile device is in a designated location, or the mobile device may delay the method until a change in location is detected.

In step 615, the mobile device 420 may detect any electronic medicament devices nearby. Mobile device 420 may use RFID, NFC, Bluetooth or another close range protocol to poll nearby tags on a medicament device. Mobile device 420 may be configured to poll one or more specific electronic medicament devices with identifiers known by mobile device 420. In step 620, mobile device 420 may determine whether an electronic medicament device is present. If no medicament device is present, the method may proceed to step 625. If a medicament device is detected, the method may proceed to step 630.

In step 625, the mobile device 420 may generate an alarm. The alarm may indicate any particular medicament device that was not detected. The alarm may include a message identifying the medicament device by name or by a condition that it treats. If the mobile device performs method 600 frequently, it may be likely that the medicament device is nearby, although out of range of the short range wireless protocol. Accordingly, a user may be reminded to retrieve the medicament device. The method may then proceed to step 660, where the method ends.

In step 630, the mobile device 420 may receive data from the medicament device. Mobile device 420 may send a read command to read data from memory 330. In various embodiments, mobile device 420 may receive data from the electronic medicament device 300 when sensor 310 determines that the device 300 has been activated. In step 635, mobile device 420 may determine whether the medicament device 300 has been used. Mobile device 420 may determine the status of sensor 310 or parse data received in step 630. If the medicament device has been used, the method may proceed to step 640. If the medicament device has not been used, the method may proceed to step 650.

In step 640, mobile device 420 may document the current location of the mobile device. In step 645, the mobile device may notify emergency contacts. Mobile device 420 may contact emergency services, for example, by dialing 911. The mobile device 420 may turn on a speaker phone to allow a user, who may be suffering from anaphylaxis or another medical condition to speak to an emergency dispatcher. If mobile device 420 does not receive any voice input, mobile device 420 may play a recorded message indicating that the electronic medicament device has been activated at the stored location. Mobile device 420 may also contact other people. For example, mobile device 420 may call, email, or message emergency contacts stored in mobile device 420 or memory 330.

In step 650, mobile device 420 may determine whether the electronic medicament device is expired. Mobile device 420 may compare an expiration date received from the electronic medicament device 300 to the current date. If the medicament device is expired, the method may proceed to step 655. If the medicament device is not expired, the method may proceed to step 650, where the method ends.

In step 655, the mobile device 655 may initiate an order for a refill or replacement electronic medicament device. Mobile device 420 may send an order to control center 450 and/or medical server 440. The method may then proceed to step 650, where the method ends.

According to the foregoing, various exemplary embodiments provide for systems and methods for distributing medicaments. In particular, by providing remote access to a medicament storage case, medicaments can be provided to patients in an emergency.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principals of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A medicament device configured to receive an epinephrine auto-injector and communicate with a mobile device associated with a designated user who requires use of the epinephrine auto-injector, the medicament device comprising:
   an electronic tag including a wireless transmitter for wireless communication, wherein the tag is configured to wirelessly communicate, with the mobile device, first information associated with the medicament device that allows for determining whether the medicament device is within close proximity to the mobile device;
   a receiver configured to wirelessly receive, from the mobile device, an identifier associated with the designated user who requires use of the epinephrine auto-injector;
   a sensor configured to detect a movement associated with a physical component of the medicament device that indicates activation of the medicament device, wherein second information associated with the activation of the medicament device is wirelessly communicated to the mobile device (i) in response to detecting the movement indicating the activation of the medicament device and (ii) subsequent to the receiver receiving the identifier associated with the designated user;

a display on the medicament device configured to illuminate; and a sound source on the medicament device configured to play a sound, wherein the electronic tag is further configured to poll or be polled by the mobile device to determine whether the medicament device is within close proximity to the mobile device from which the identifier associated with the designated user was received, and wherein, in response to the medicament device not being within close proximity to the mobile device from which the identifier associated with the designated user of the epinephrine auto-injector was received, at least one of (i) the display illuminates and (ii) the sound source plays the sound.

2. The medicament device of claim 1, further comprising a processor connected to the electronic tag and the sensor.

3. The medicament device of claim 1, further comprising a global positioning system receiver, wherein the global positioning system receiver is configured to generate third information associated with a location of the medicament device, and wherein the electronic tag is further configured to wirelessly communicate the third information to the mobile device.

4. The medicament device of claim 1, wherein the electronic tag comprises a memory configured to store at least information received from the mobile device.

5. The medicament device of claim 1, wherein the electronic tag comprises a Bluetooth wireless transmitter.

6. The medicament device of claim 1, wherein the sensor comprises a frangible element that completes or breaks when the medicament device is being used.

7. The medicament device of claim 1, further comprising a door coupled with the medicament device and configured to move between an open position and a closed position, wherein in the open position the epinephrine auto-injector can be loaded into the medicament device and removed therefrom, and wherein in the closed position the epinephrine auto-injector cannot be loaded into the medicament device or removed therefrom.

8. The medicament device of claim 1, wherein the display comprises a flashing display.

9. A non-transitory computer readable medium comprising instructions stored thereon that when executed by at least one processor of a mobile device perform a process for monitoring a medicament device, the process comprising:

identifying a user who is associated with the mobile device and who requires use of an epinephrine auto-injector;

wirelessly communicating with the medicament device based on the medicament device containing the epinephrine auto-injector required by the user associated with the mobile device, wherein wirelessly communicating with the medicament device comprises the mobile device communicating, to the medicament device, an identifier associated with the user who requires use of the epinephrine auto-injector;

based at least on the wireless communication and identifying the user who requires the use of the epinephrine auto-injector, determining whether the medicament device is within close proximity to the mobile device and generating an alert on the mobile device in response to determining that the medicament device is not within close proximity to the mobile device;

based at least on the wireless communication, determining whether a movement associated with a physical component of the medicament device has occurred that indicates that the medicament device is being used or has been used; and notifying emergency contacts through the mobile device in response to determining that the movement has occurred that indicates that the medicament device is being used or has been used.

10. The non-transitory computer readable medium of claim 9, wherein determining whether the medicament device is within close proximity to the mobile device comprises transmitting from the mobile device a first communication associated with a location of the mobile device, wherein the first communication is intended to be received by the medicament device.

11. The non-transitory computer readable medium of claim 10, wherein determining whether the medicament device is within close proximity to the mobile device further comprises:

determining whether a second communication was received from the medicament device, wherein the second communication is associated with the location of the medicament device; and generating the alert in response to determining that the second communication was not received from the medicament device.

12. The non-transitory computer readable medium of claim 9, wherein determining whether the medicament device is being used or has been used comprises receiving a communication from the medicament device indicating that the medicament device is being used or has been used.

13. The non-transitory computer readable medium of claim 9, wherein the process further comprises generating an additional alert with the mobile device if the medicament device is being used or has been used.

14. The non-transitory computer readable medium of claim 9, wherein the process further comprises generating an additional alert with the mobile device if the epinephrine auto-injector has expired.

15. A system for monitoring a medicament device with a mobile device associated with a designated user of an epinephrine auto-injector, the system comprising:

the medicament device for receiving the epinephrine auto-injector, the medicament device comprising:

a sensor configured to detect an event associated with the medicament device, the event comprising a movement associated with a physical component of the medicament device; and a communication interface configured to receive, from the mobile device, an identifier associated with the designated user and to wirelessly communicate, with the mobile device, information associated with the medicament device subsequent to receiving the identifier; and a non-transitory computer readable medium comprising instructions stored thereon that when executed by at least one processor of the mobile device perform a process comprising:

identifying the user who is associated with the mobile device and who requires use of the epinephrine auto-injector;

wirelessly communicating with the medicament device based on an identification of the user who requires use of the epinephrine auto-injector;

based at least on the wireless communication, determining whether the medicament device is within close proximity to the mobile device;

based at least on the wireless communication, determining whether the event associated with the medicament device has occurred; and generating one or more alerts on the mobile device if the medicament device is determined not to be within close proximity to the mobile device or if the event associated with the medicament device has occurred.

16. The system of claim 15, wherein the sensor is configured to detect whether the medicament device is being used or has been used, and the process comprises generating an alert on the mobile device based on receiving information via the communication interface that the medicament device is being used or has been used.

17. The system of claim 15, wherein the process further comprises notifying emergency contacts through the mobile device if it has been determined that the medicament device is being used or has been used.

18. The system of claim 15, wherein determining whether the medicament device is within close proximity to the mobile device is based on information transmitted via the communication interface from the medicament device to the mobile device.

19. The non-transitory computer readable medium of claim 9, wherein the process further comprises determining a location of the medicament device.

20. The non-transitory computer readable medium of claim 19, wherein the process further comprises displaying a map indicating the location of the medicament device.

* * * * *